United States Patent [19]

Theodoridis

[11] Patent Number: 4,898,606
[45] Date of Patent: Feb. 6, 1990

[54] PHOSPHORYLAMINOPHENYLTRIAZOLI-NONE HERBICIDES

[75] Inventor: George Theodoridis, Princeton, N.J.

[73] Assignee: FMC Corporation, Philadelphia, Pa.

[21] Appl. No.: 319,842

[22] Filed: Mar. 7, 1989

Related U.S. Application Data

[63] Continuation-in-part of Ser. No. 258,292, Oct. 14, 1988, abandoned.

[51] Int. Cl.$^4$ .......................... A01N 57/32; C07F 9/65
[52] U.S. Cl. ........................................ 71/86; 548/112
[58] Field of Search ............................ 548/112; 71/86

[56] References Cited

U.S. PATENT DOCUMENTS

| | | | |
|---|---|---|---|
| 4,560,752 | 12/1985 | Lee | 544/66 |
| 4,613,675 | 9/1980 | Lee | 71/86 |
| 4,777,163 | 10/1988 | Bosies et al. | 548/112 X |

FOREIGN PATENT DOCUMENTS

| | | |
|---|---|---|
| 59-933293 | 2/1984 | Japan . |
| 60-228494 | 11/1985 | Japan . |
| 60-246392 | 12/1985 | Japan . |
| 61-103887 | 5/1986 | Japan . |

OTHER PUBLICATIONS

Derwent Abstracts, accession No. 86-172208/27 (1986), abstract of reference D above.
Derwent Abstracts, accession No. 86-024718/04 (1986), abstract of reference E above.
Chemical Abstracts, 104, 149, 169k (1986), abstract of reference E above.
Chemical Abstracts, 104, 149, 168j (1986), abstract of reference F above.
Derwent Abstracts, accession No. 86-003058/01 (1986), abstract of reference F above.
Derwent Abstracts, accession No. 84-084466/14 (1984), abstract of reference G above.
Derwent Abstracts, accession No. 88-127,433/19 (1988), abstract of W. German DE 3737-152-A (Ciba Geigy), published 5-5-88.
Derwent Abstracts, accession No. 87-362698/51 (1987), abstract of World Patent WO 87/07602 (Rhone Poulenc), published 12-18-87.
Derwent Abstracts, accession No. 85-204,356/34 (1985), abstract of DE 3504051 (Sandoz), published 8-14-85.

Primary Examiner—Richard L. Raymond
Attorney, Agent, or Firm—Robert M. Kennedy; H. Robinson Ertelt; Abner Sheffer

[57] ABSTRACT

The present application discloses herbicidal phosphorylaminophenyltriazolinones, compositions of them, methods of preparing them, and methods for controlling undesired plant growth by preemergence or postemergence application of the herbicidal compositions to the locus where control is desired. The herbicidal compounds are compounds of the formula

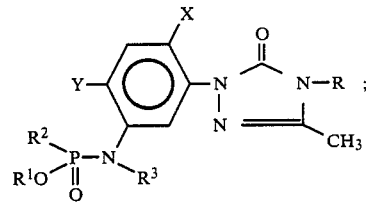

in which X and Y are independently F, Cl, or Br; R is lower alkyl or lower haloalkyl; $R^1$ is selected from lower alkyl, lower haloalkyl, cycloalkyl or 3 to 7 ring carbon atoms, lower alkenyl, lower haloalkenyl, lower alkynyl, lower haloalkynyl, and benzyl which is unsubstituted or substituted on the phenyl ring with one or more substituents selected from halogen, lower alkyl, lower alkoxy, lower alkoxycarbonyl, cyano, and nitro; $R^2$ is independently selected from among —$OR^1$ or is hydroxy, amino, lower alkylamino, or lower dialkylamino; $R^3$ is H, lower alkyl, or lower alkenyl or a base addition salt of the compound as defined above in which $R^2$ is hydroxy.

21 Claims, No Drawings

PHOSPHORYLAMINOPHENYLTRIAZOLINONE HERBICIDES

This application is a continuation-in-part of application Ser. No. 258,292, filed 10/14/88, now abandoned.

The invention described in this application pertains to weed control in agriculture, horticulture, and other fields where there is a desire to control unwanted plant growth. More specifically, the present application describes certain herbicidal phosphorylaminophenyltriazolinones, compositions of them, methods of preparing them, and methods for controlling undesired plant growth by preemergence or postemergence application of the herbicidal compositions to the locus where control is desired. The present compounds may be used to effectively control a variety of both grassy and broadleaf plant species.

U.S. Pat. No. 4,613,675 discloses, as intermediates for herbicidal compounds, aryltetrahydrophthalimides of the formula

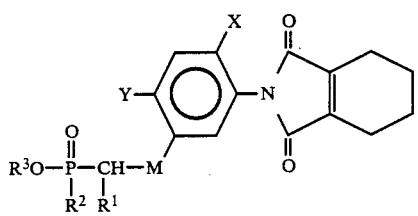

in which each of X and Y is independently hydrogen or halogen, M is oxygen, sulfur, sulfinyl, sulfonyl, or N-R, each of R and $R^1$ is independently hydrogen or lower alkyl, $R^2$ is lower alkyl, and $R^3$ is lower alkyl, alkoxyalkyl, or alkoxycarbonylalkyl.

Japanese Kokai 61-103,887, published May 22, 1986, discloses (as reported in Derwent Abstracts, accession No. 86-172208/27) herbicidal compounds of the formula

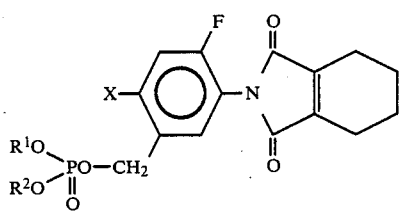

in which X is chlorine or bromine and $R^1$ and $R^2$ are independently 1-4C alkyl. Japanese Kokai 60-246,392, published Dec. 6, 1985, discloses (as reported in Chemical Abstracts, 104, 149,169k, 1986) herbicidal compounds of the formula

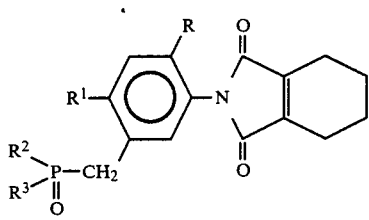

in which R is hydrogen or fluorine, $R^1$ is chlorine or bromine, and $R^2$ and $R^3$ are chlorine, hydroxy, alkyl, alkoxy, alkenyloxy, or alkylamino.

Japanese Kokai 60-228,494, published Nov. 13, 1985, discloses (as reported in Derwent Abstracts, accession No. 86-003058/01) herbicidal compounds of the formula

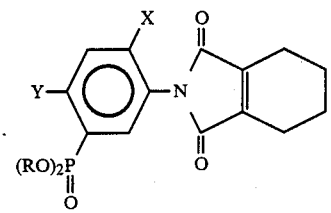

in which X is hydrogen, fluorine, or chlorine, Y is chlorine or bromine, and R is hydrogen or 1-4C alkyl.

Japanese Kokai 59-033,293, published Feb. 23, 1984, discloses (as reported in Derwent Abstracts, accession No. 84-084464/14) herbicidal compounds of the formula

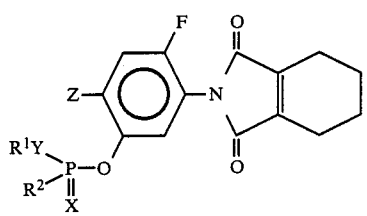

in which X is oxygen or sulfur, Y is oxygen, sulfur, or amino, Z is halogen, $R^1$ is alkyl or alkoxyalkoxyalkyl, and $R^2$ is alkyl, alkoxy, haloalkyl, alkoxyalkoxyalkoxy, or phenyl.

The herbicidal compounds of the present invention are compounds of the formula

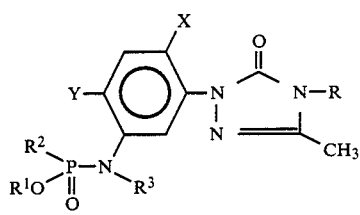

in which:

X and Y are independently F, Cl, or Br;

R is lower alkyl (e.g. —$CH_3$) or lower haloalkyl (e.g. —$CHF_2$ or —$CH_2CH_2CH_2F$);

$R^1$ is selected from lower alkyl (e.g. —$CH_3$ or —$CH(CH_3)CH_2CH_3$), lower haloalkyl (e.g. —$CH_2CH_2Cl$), cycloalkyl of 3 to 7 ring carbon atoms (e.g. cyclopentyl), lower alkenyl (e.g. —$CH_2CH=CH_2$), lower haloalkenyl (e.g. —$CH_2C(Cl)=CH_2$), lower alkynyl (e.g. —$CH_2C\equiv CH$), lower haloalkynyl (e.g. —$CH_2C\equiv CBr$), and benzyl which may be substituted on the phenyl ring with one or more substituents selected from halogen, lower alkyl, lower alkoxy, lower alkoxycarbonyl, cyano, and nitro;

$R^2$ is independently selected from among —$OR^1$ or is hydroxy, amino, lower alkylamino (e.g. —$NHC_2H_5$), or lower dialkylamino (e.g. —$N(CH_3)C_2H_5$); or a base addition salt of the compound as defined above in which $R^2$ is hydroxy.

$R^3$ is hydrogen, alkyl (e.g., lower alkyl such as —$CH_3$), or alkenyl (e.g., lower alkenyl such as —$CH_2CH=CH_2$).

It is often preferable that any alkyl group or alkyl portion of any group herein have 1–6 carbon atoms and that any alkenyl or alkynyl group or alkenyl or alkynyl portion of any group herein have 3–6 carbon atoms.

The substituent X is advantageously F or Cl, preferably F. Y is preferably Cl or Br, more preferably Cl. In preferred embodiments X is F and Y is Cl, X is F and Y is Br, or X and Y are both Cl.

The R substituent is preferably a haloalkyl group, e.g., a lower fluoroalkyl group such as $CHF_2$.

Compounds in which $R^2$ is hydroxy are acidic and form herbicidal base addition salts upon treatment with a base. Typical cations of such salts include sodium, potassium, calcium, ammonium, magnesium, and mono-, di-, and tri ($C_1$–$C_4$ alkyl) ammonium, sulfonium, or sulfoxonium ions.

The compounds of this invention may be prepared by the use of steps generally described in the literature or by methods analogous or similar thereto and within the skill of the art.

A useful intermediate in preparing the present compounds is a compound of the formula

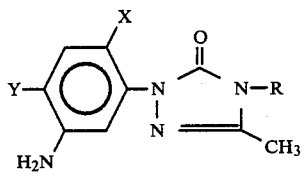

II in which X, Y, and R are as defined above.

The intermediate amino compound II may be converted into final products I by known general methods, for example by a method similar to that described by R. M. Caven, J. Chem. Soc. 81, 1362 (1902). For example, II may be treated with a phosphoryl dihalide containing the $R^2$ group (or —$OR^1$ group), in the presence of a base (e.g. triethylamine) to produce a halophosphoramide derivative of II, followed by reaction with $R^1$—OH (or $R^2H$) in the presence of a base to give final product I where $R^3$ is H, as illustrated in the following chemical equations:

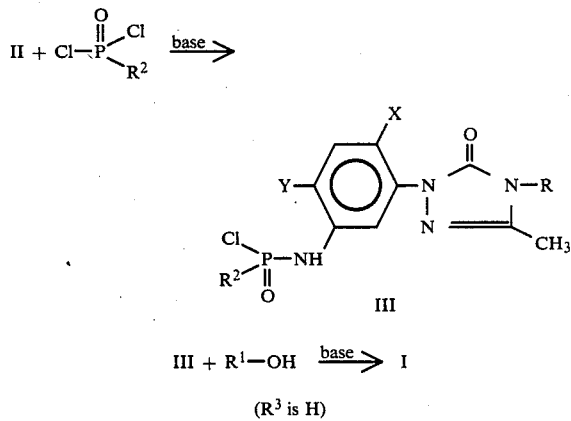

III + $R^1$—OH $\xrightarrow{\text{base}}$ I ($R^3$ is H)

The compounds in which $R^3$ is alkyl or alkenyl may be prepared by alkylating or alkenylating the corresponding componding compounds in which $R^3$ is H, for example by treating the compound in which $R^3$ is H with a base (such as sodium hydride) in the presence of an inert solvent (such as dimethylformamide) followed by treatment with $R^3$—Z in which Z is good leaving group (such as Cl, Br, or I).

A particularly useful alternative method for producing the products of formula I in which $R^2$ is the same as $OR^1$ and $R^3$ is H comprises reacting the amine intermediate (II) with a phosphorus oxyhalide, such as $POCl_3$, followed by treatment of the resulting dihalophosphoramide derivative with at least 2 equivalents of $R^1$—OH in the presence of a base (e.g. $NaHCO_3$).

The intermediates of general formula II include a number of previously described compounds and may be prepared by methods disclosed in the art for those known compounds or by methods analogous thereto. For example, Example 1 of PCT Patent Application Publication No. WO87/03782, published July 2, 1987, describes the preparation of the compound of formula II above in which X is F, Y is Cl, and R is $CHF_2$, Example 8 describes the preparation of the corresponding compound in which Y is Br, Example 11 describes preparation of the compound in which X is F, Y is Cl, and R is $CH_3$, and Example 13 describes preparation of the compound in which X and Y are each Cl and R is $CHF_2$.

Representative compounds of the invention are shown in Table 1 below. Herbicidal data are given in Tables 3 and 4 below. In Tables 3 and 4, the abbreviation "kg/ha" means kilograms per hectare.

Preparation of the compounds of this invention is further illustrated in the following Examples.

EXAMPLE 1

1-[4—CHLORO-2-FLUORO-5-(0,0-DIETHYL-PHOSPHORYLAMINO)PHENYL]-4-DIFLUOROMETHYL-4,5-DIHYDRO-3-METHYL-1,2,4-TRIAZOL-5(1H)-ONE

A stirred mixture of 1.0 g (0.0041 mole) of 1-(5-amino-4-chloro-2-fluorophenyl)-4-difluoromethyl-4,5-dihydro-3-methyl-1,2,4-triazol-5(1H)-one in 10 mL of phosphorus oxychloride was heated at reflux for approximately 18 hours. The reaction mixture was cooled, and the excess phosphorus oxychloride was removed by distillation under reduced pressure, leaving an oil. The oil was dissolved in approximately 10 mL of ethanol, and solid sodium bicarbonate was added until a neutral mixture was obtained. The mixture was filtered, and the filtrate was evapoated under reduced pressure leaving a residue. The residue was purified first by column chromatography on silica gel, eluting with methylene chloride:acetone (80:20), then by recrystallization from n-heptane:ethyl acetate (95:5) to give 0.25 g of 1-[4-chloro-2-fluoro-5-(0,0-diethylphosphorylamino)-phenyl]-4-difluoromethyl-4,5-dihydro-3-methyl-1,2,4-triazol-5(1H)-one, m.p. 96°–97° C., compound 1 of Table 1 below.

The nmr and ir spectra were consistent with the proposed structure.

EXAMPLE 2

1-[4-CHLORO-2-FLUORO-5-(0,0-DIMETHYL-PHOSPHORYL-AMINO)PHENYL]-4-DIFLOROMETHYL-4,5-DIHYDRO-3-METHYL-1,2,4-TRIAZOL-5(1H)-ONE

In a manner similar to that described in Example 1, treatment of 1-(5-amino-4-chloro-2-fluorophenyl)-4-difluoromethyl-4,5-dihydro-3-methyl-1,2,4-triazol-5(1H)-one with phosphorus oxychloride, followed by treatment with methanol produced the desired product, m.p. 134°–136° C., compound 2 of Table 1 below.

The nmr and ir spectra were consistent with the proposed structure.

HERBICIDAL ACTIVITY

The plant test species used in demonstrating the herbicidal activity of compounds of this invention include cotton (*Gossyoium hirsutum* var. DPLGI), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea acumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum haleoense*).

Preparation of Flats
Preemergence:

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below. Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Rating Percent Control | Description of Main Categories | Crop Description | Weed Description |
| --- | --- | --- | --- |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by wight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl- | |

| Component: | % by Wt. |
|---|---|
| naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific example of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |

| Component: | % by Wt. |
|---|---|
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

250 g/ha, preferably about 4 to 30 g/ha. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

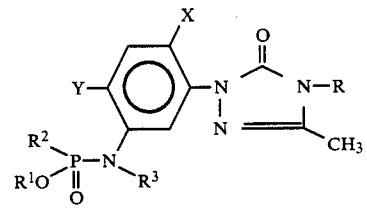

| Cmpd. No. | X | Y | OR¹ | R² | R | R³ |
|---|---|---|---|---|---|---|
| 1 | F | Cl | OC₂H₅ | OC₂H₅ | CHF₂ | H |
| 2 | F | Cl | OCH₃ | OCH₃ | CHF₂ | H |
| 3 | F | Cl | OC₃H₇(n) | OC₃H₇(n) | CHF₂ | H |

TABLE 1-continued

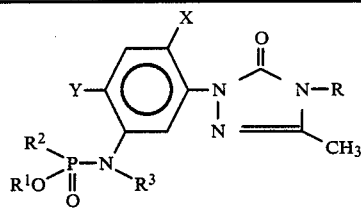

| Cmpd. No. | X | Y | OR$^1$ | R$^2$ | R | R$^3$ |
|---|---|---|---|---|---|---|
| 4 | F | Cl | OCH(CH$_3$)$_2$ | OCH(CH$_3$)$_2$ | CHF$_2$ | H |
| 5 | F | Cl | OCH$_2$CH(CH$_3$)$_2$ | OCH$_2$CH(CH$_3$)$_2$ | CHF$_2$ | H |
| 6 | F | Cl | OCH(CH$_3$)CH$_2$CH$_3$ | OCH(CH$_3$)CH$_2$CH$_3$ | CHF$_2$ | H |
| 7 | F | Cl | OCH$_3$ | OCH(CH$_3$)CH$_2$CH$_3$ | CHF$_2$ | H |
| 8 | F | Cl | OCH$_2$CH$_2$Cl | OC$_3$H$_7$(n) | CHF$_2$ | H |
| 9 | Cl | Cl | OCF$_3$ | OCF$_3$ | CF$_3$ | H |
| 10 | F | Cl | OC$_2$H$_5$ | OCH$_2$CH=CH$_2$ | CH$_3$ | H |
| 11 | Cl | Cl | OCH(CH$_3$)$_2$ | OCH$_2$C(Cl)=CH$_2$ | CHF$_2$ | H |
| 12 | F | Br | OCH$_2$CH=CH$_2$ | OCH$_2$CH=CH$_2$ | CH$_2$CH$_2$CH$_2$F | H |
| 13 | F | Cl | OC$_3$H$_7$(n) | O—cyclopropyl | CHF$_2$ | H |
| 14 | Cl | Cl | OC$_2$H$_5$ | O—cyclopentyl | CH$_2$F | H |
| 15 | F | Cl | OCH$_3$ | OCH$_2$C≡CH | CHF$_2$ | H |
| 16 | F | Br | OCH$_3$ | OCH$_2$C≡CBr | CHF$_2$ | H |
| 17 | Cl | Cl | OCH$_2$C≡CH | OCH$_2$C≡CH | CHF$_2$ | H |
| 18 | F | Cl | OCH$_2$C$_6$H$_5$ | OCH$_2$C$_6$H$_5$ | CHF$_2$ | H |
| 19 | Cl | Cl | OC$_2$H$_5$ | OCH$_2$C$_6$H$_4$—4-Cl | CHF$_2$ | H |
| 20 | F | Cl | OC$_2$H$_5$ | OCH$_2$C$_6$F$_5$ | CHF$_2$ | H |
| 21 | F | Cl | OCH$_3$ | OCH$_2$C$_6$H$_4$—4-CH$_3$ | CHF$_2$ | H |
| 22 | F | Cl | OCH$_3$ | OCH$_2$C$_6$H$_4$—3-NO$_2$ | CHF$_2$ | H |
| 23 | F | Cl | OC$_2$H$_5$ | OCH$_2$C$_6$H$_4$—3-CN | CHF$_2$ | H |
| 24 | F | Cl | OCH$_3$ | OCH$_2$C$_6$H$_4$—3-CO$_2$CH$_3$ | CHF$_2$ | H |
| 25 | F | Cl | OC$_2$H$_5$ | OCH$_2$C$_6$H$_3$—2,4(OCH$_3$)$_2$ | CHF$_2$ | H |
| 26 | F | Cl | OCH(CH$_3$)$_2$ | OH | CH$_2$CH$_2$CH$_2$F | H |
| 27 | Cl | Cl | OCH$_3$ | NH$_2$ | CHF$_2$ | H |
| 28 | Cl | Cl | OCH$_3$ | NHCH$_3$ | CHF$_2$ | H |
| 29 | Cl | Cl | OCH$_3$ | N(C$_2$H$_5$)$_2$ | CHF$_2$ | H |
| 30 | F | Cl | OC$_2$H$_5$ | NHC$_2$H$_5$ | CHF$_2$ | H |
| 31 | F | Cl | OC$_2$H$_5$ | N(CH$_3$)C$_2$H$_5$ | CHF$_2$ | H |
| 32 | F | Cl | OCH(CH$_3$)$_2$ | O$^-$Na$^+$ | CH$_2$CH$_2$CH$_2$F | H |
| 33 | Cl | Cl | OCH$_3$ | OH | CHF$_2$ | H |
| 34 | Cl | Cl | OCH$_3$ | O$^-$K$^+$ | CHF$_2$ | H |
| 35 | Cl | Cl | OCH$_3$ | OCH$_3$ | CHF$_2$ | CH$_3$ |
| 36 | Cl | Cl | OCH$_3$ | OCH$_3$ | CHF$_2$ | C$_2$H$_5$ |
| 37 | Cl | Cl | OCH$_3$ | OCH$_3$ | CHF$_2$ | C$_3$H$_7$(n) |
| 38 | F | Cl | OCH$_3$ | OCH$_3$ | CHF$_2$ | CH$_3$ |
| 39 | F | Cl | OCH$_3$ | OCH$_3$ | CHF$_2$ | C$_2$H$_5$ |
| 40 | F | Cl | OCH$_3$ | OCH$_3$ | CHF$_2$ | C$_3$H$_7$(n) |
| 41 | F | Cl | OCH$_3$ | OCH$_3$ | CHF$_2$ | CH(CH$_3$)$_2$ |
| 42 | Cl | Cl | OCH$_3$ | OCH$_3$ | CHF$_2$ | CH(CH$_3$)$_2$ |
| 43 | F | Cl | OCH$_3$ | OCH$_3$ | CHF$_2$ | C$_4$H$_9$(n) |
| 44 | F | Cl | OCH$_3$ | OCH$_3$ | CHF$_2$ | CH$_2$CH=CH$_2$ |
| 45 | F | Cl | OCH$_3$ | OCH$_3$ | CHF$_2$ | C$_7$H$_{15}$(n) |
| 46 | Cl | Cl | OCH$_3$ | OCH$_3$ | CHF$_2$ | C$_4$H$_9$(n) |
| 47 | Cl | Cl | OCH$_3$ | OCH$_3$ | CHF$_2$ | CH$_2$CH=CH$_2$ |
| 48 | Cl | Cl | OCH$_3$ | OCH$_3$ | CHF$_2$ | C$_7$H$_{15}$(n) |
| 49 | Cl | Cl | OCH$_3$ | OCH$_3$ | CHF$_2$ | CH$_3$ |
| 50 | F | Cl | OCH$_3$ | OCH$_3$ | CHF$_2$ | C$_2$H$_5$ |

What is claimed:

TABLE 2

Characterizing Data

| Cmpd. No. | mp (°C.) | Cmpd. No. | mp (°C.) |
|---|---|---|---|
| 1 | 96–97 | 41 | 89–92 |
| 2 | 134–136 | 42 | oil |
| 35 | 125–128 | 43 | oil |
| 36 | 104–107 | 44 | 99–101 |
| 37 | oil | 45 | oil |
| 38 | 138–141 | 46 | oil |
| 39 | 107–109 | 47 | oil |
| 40 | 92-5–95 | 48 | oil |

TABLE 3
PREEMERGENCE HERBICIDAL ACTIVITY (% CONTROL)

| Compound No. | 1 | 2 | 35 | 36 |
|---|---|---|---|---|
| Rate (kg/ha) | 2.0 | 2.0 | 0.5 | 0.5 |
| Species | | | | |
| Cotton | 100 | 100 | 30 | 70 |
| Soybean | 100 | 100 | 70 | 90 |
| Field Corn | 100 | 100 | 90 | 95 |
| Rice | 100 | 100 | 10 | 85 |
| Wheat | 100 | 100 | 40 | 95 |
| Morningglory | 100 | 100 | 70 | 90 |
| Wild Mustard | 100 | 100 | 80 | 90 |
| Velvetleaf | 100 | 100 | 100 | 100 |
| Barnyardgrass | 100 | 100 | 40 | 95 |
| Green Foxtail | 100 | 100 | 95 | 100 |
| Johnsongrass | 100 | 100 | 70 | 95 |
| Compound No. | 37 | 38 | 39 | 40 |
| Rate (kg/ha) | 0.5 | 0.25 | 0.25 | 0.25 |

TABLE 3-continued

| Species | | | | |
|---|---|---|---|---|
| Cotton | 70 | 70 | 90 | 95 |
| Soybean | 100 | 100 | 100 | 100 |
| Field Corn | 95 | 70 | 100 | 100 |
| Rice | 70 | 20 | 95 | 90 |
| Wheat | 90 | 40 | 100 | 100 |
| Morningglory | 100 | 95 | 95 | 100 |
| Wild Mustard | 100 | 95 | 100 | 100 |
| Velvetleaf | 100 | 100 | 100 | 100 |
| Barnyardgrass | 95 | 80 | 100 | 100 |
| Green Foxtail | 100 | 100 | 100 | 100 |
| Johnsongrass | 100 | 100 | 100 | 100 |

| Compound No. | 41 | 42 | 43 | 44 |
|---|---|---|---|---|
| Rate (kg/ha) | 0.25 | 0.25 | 0.25 | 0.25 |

| Species | | | | |
|---|---|---|---|---|
| Cotton | 85 | 50 | 70 | 100 |
| Soybean | 100 | 30 | 100 | 100 |
| Field Corn | 95 | 80 | 100 | 100 |
| Rice | 95 | 80 | 80 | 95 |
| Wheat | 100 | 30 | 90 | 100 |
| Morningglory | 100 | 80 | 100 | 100 |
| Wild Mustard | 100 | 100 | 100 | 100 |
| Velvetleaf | 100 | 100 | 100 | 100 |
| Barnyardgrass | 100 | 85 | 100 | 95 |
| Green Foxtail | 100 | 100 | 100 | 100 |
| Johnsongrass | 100 | 95 | 100 | 100 |

| Compound No. | 45 | 46 | 47 | 48 |
|---|---|---|---|---|
| Rate (kg/ha) | 0.25 | 0.25 | 0.25 | 0.25 |

| Species | | | | |
|---|---|---|---|---|
| Cotton | 70 | 15 | 20 | 0 |
| Soybean | 70 | 0 | 70 | 5 |
| Field Corn | 95 | 15 | 100 | 0 |
| Rice | 85 | 0 | 80 | 0 |
| Wheat | 70 | 10 | 85 | 5 |
| Morningglory | 95 | 10 | 70 | 5 |
| Wild Mustard | 100 | 95 | 100 | 50 |
| Velvetleaf | 100 | 100 | 100 | 40 |
| Barnyardgrass | 90 | 95 | 90 | 0 |
| Green Foxtail | 100 | 95 | 100 | 30 |
| Johnsongrass | 100 | 95 | 100 | 5 |

TABLE 4

POSTEMERGENCE HERBICIDAL ACTIVITY (% CONTROL)

| Compound No. | 1 | 2 | 35 | 36 |
|---|---|---|---|---|
| Rate (kg/ha) | 2.0 | 2.0 | 0.5 | 0.5 |

| Species | | | | |
|---|---|---|---|---|
| Cotton | 100 | 100 | 100 | 100 |
| Soybean | 100 | 100 | 85 | 90 |
| Field Corn | 100 | 100 | 100 | 100 |
| Rice | 100 | 100 | 70 | 85 |
| Wheat | 100 | 100 | 50 | 80 |
| Morningglory | 100 | 100 | 95 | 100 |
| Wild Mustard | 100 | 100 | 30 | 70 |
| Velvetleaf | 100 | 100 | 100 | 100 |
| Barnyardgrass | 100 | 100 | 40 | 95 |
| Green Foxtail | 100 | 100 | 100 | 100 |
| Johnsongrass | 100 | 100 | 100 | 95 |

| Compound No. | 37 | 38 | 39 | 39 |
|---|---|---|---|---|
| Rate (kg/ha) | 0.5 | 0.25 | 0.25 | 0.25 |

| Species | | | | |
|---|---|---|---|---|
| Cotton | 100 | 85 | 100 | 100 |
| Soybean | 95 | 95 | 100 | 100 |
| Field Corn | 100 | 80 | 95 | 100 |
| Rice | 80 | 30 | 95 | 95 |
| Wheat | 95 | 90 | 100 | 100 |
| Morningglory | 100 | 100 | 100 | 100 |
| Wild Mustard | 90 | 70 | 100 | 95 |
| Velvetleaf | 100 | 100 | 100 | 100 |
| Barnyardgrass | 95 | 95 | 95 | 95 |
| Green Foxtail | 100 | 95 | 100 | 100 |
| Johnsongrass | 100 | 100 | 100 | 100 |

| Compound No. | 41 | 42 | 43 | 44 |
|---|---|---|---|---|
| Rate (kg/ha) | 0.25 | 0.25 | 0.25 | 0.25 |

TABLE 4-continued

| Species | | | | |
|---|---|---|---|---|
| Cotton | 100 | 90 | 90 | 100 |
| Soybean | 95 | 90 | 95 | 95 |
| Field Corn | 100 | 20 | 70 | 100 |
| Rice | 100 | 20 | 70 | 100 |
| Wheat | 100 | 50 | 90 | 100 |
| Morningglory | 100 | 100 | 100 | 100 |
| Wild Mustard | 95 | 30 | 90 | 95 |
| Velvetleaf | 100 | 100 | 100 | 100 |
| Barnyardgrass | 100 | 50 | 95 | 100 |
| Green Foxtail | 100 | 70 | 100 | 100 |
| Johnsongrass | 100 | 95 | 100 | 100 |

| Compound No. | 45 | 46 | 47 | 48 |
|---|---|---|---|---|
| Rate (kg/ha) | 0.25 | 0.25 | 0.25 | 0.25 |

| Species | | | | |
|---|---|---|---|---|
| Cotton | 100 | 80 | 95 | 80 |
| Soybean | 95 | 85 | 90 | 80 |
| Field Corn | 100 | 95 | 95 | 85 |
| Rice | 70 | 10 | 70 | 5 |
| Wheat | 90 | 50 | 80 | 20 |
| Morningglory | 100 | 85 | 100 | 100 |
| Wild Mustard | 90 | 10 | 90 | 50 |
| Velvetleaf | 100 | 100 | 100 | 90 |
| Barnyardgrass | 85 | 30 | 80 | 40 |
| Green Foxtail | 95 | 30 | 100 | 60 |
| Johnsongrass | 100 | 50 | 100 | 30 |

1. A compound of the formula in which

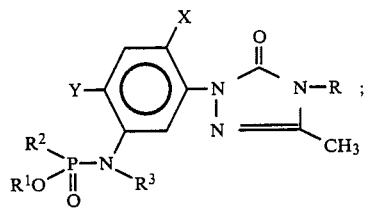

X and Y are independently F, Cl, or Br;
R is lower alkyl or lower haloalkyl;
$R^1$ is selected from lower alkyl, lower haloalkyl, cycloalkyl of 3 to 7 ring carbon atoms, lower alkenyl, lower haloalkenyl, lower alkynyl, lower haloalkynyl, and benzyl which is unsubstituted or substituted on the phenyl ring with one or more substituents selected from halogen, lower alkyl, lower alkoxy, lower alkoxycarbonyl, cyano, and nitro;
$R^2$ is independently selected from among $-OR^1$ or is hydroxy, amino, lower alkylamino, or lower dialkylamino;
$R^3$ is H, lower alkyl, or lower alkenyl; or a base addition salt of the compound as defined above in which $R^2$ is hydroxy.

2. The compound of claim 1 in which R is a lower fluoroalkyl group.

3. The compound of claim 2 in which X and Y are respectively F, Cl; Cl, Cl; or F, Br.

4. The compound of claim 3 in which R is $-CHF_2$.

5. The compound of claim 4 in which X and Y are respectively F,Cl or Cl,Cl.

6. The compound of claim 5 in which $R^2$ is hydroxy, amino, lower alkylamino, or lower dialkylamino; or a base addition salt of the compound in which $R^2$ is hydroxy.

7. The compound of claim 6 in which $R^1$ is lower alkyl.

8. The compound of claim 5 in which $R^2$ is independently selected from among $-OR^1$.

9. The compound of claim 8 in which $R^1$ is lower alkyl.

10. The compound of claim 9 in which $R^2$ is the same as $-OR^1$.

11. The compound of claim 1 in which $R^3$ is H.

12. The compound of claim 7 in which $R^3$ is H.

13. The compound of claim 9 in which $R^3$ is H.

14. The compound of claim 1 in which $R^3$ is lower alkyl.

15. The compound of claim 7 in which $R^3$ is lower alkyl.

16. The compound of claim 9 in which $R^3$ is lower alkyl.

17. The compound of claim 1 in which $R^3$ is lower alkenyl.

18. The compound of claim 1 in which $R^3$ is lower alkenyl.

19. The compound of claim 1 in which $R^3$ is lower alkenyl.

20. A herbicidal composition comprising an herbicidally effective amount of the compound of claim 1 in admixture with a suitable carrier.

21. A method for controlling undesired plant growth which comprises applying to the locus where control is desired a herbicidally effective amount of the composition of claim 20.

* * * * *